(12) United States Patent
Moradi et al.

(10) Patent No.: US 10,766,859 B2
(45) Date of Patent: Sep. 8, 2020

(54) CATALYTIC HYDROGENATION OF NITRILES

(71) Applicant: BAYER CROPSCIENCE AKTIENGESELLSCHAFT, Monheim am Rhein (DE)

(72) Inventors: Wahed Ahmed Moradi, Monheim (DE); Thomas Himmler, Odenthal (DE); Thomas Norbert Mueller, Wehr (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 16/471,144

(22) PCT Filed: Dec. 18, 2017

(86) PCT No.: PCT/EP2017/083321
§ 371 (c)(1),
(2) Date: Jun. 19, 2019

(87) PCT Pub. No.: WO2018/114810
PCT Pub. Date: Jun. 28, 2018

(65) Prior Publication Data
US 2020/0039936 A1  Feb. 6, 2020

(30) Foreign Application Priority Data
Dec. 21, 2016 (EP) .................... 16205582

(51) Int. Cl.
*C07D 213/26* (2006.01)
*C07D 213/40* (2006.01)
*C07D 213/60* (2006.01)
*C07D 213/61* (2006.01)

(52) U.S. Cl.
CPC ......... *C07D 213/26* (2013.01); *C07D 213/40* (2013.01)

(58) Field of Classification Search
CPC .. C07D 213/26; C07D 213/40; C07D 213/60; C07D 213/61
See application file for complete search history.

(56) References Cited

U.S. PATENT DOCUMENTS

| 7,572,818 B2 | 8/2009 | Mansfield et al. |
| 7,777,045 B2 | 8/2010 | Lhermitte et al. |
| 8,148,536 B2 | 4/2012 | Shigemura et al. |
| 2012/0094983 A1 | 4/2012 | Johnson et al. |

FOREIGN PATENT DOCUMENTS

| EP | 1674455 A1 | 6/2006 |
| EP | 2371814 A1 | 10/2011 |
| WO | 2004/016088 A2 | 2/2004 |
| WO | 2004/041210 A2 | 5/2004 |
| WO | 2008/125839 A2 | 10/2008 |
| WO | 2011/047156 A1 | 4/2011 |

OTHER PUBLICATIONS

Donaldson, J.D., Ullmann's Encyclopedia of Industrial Chemistry 2012 vol. 9 Cobalt and Cobalt Compounds p. 429-465.*
International Search Report of International Patent Application No. PCT/EP2017/083321 dated Jan. 25, 2018.
Skerlj, et al., "Palladium(0)-Catalyzed Coupling of Organozinc Iodide Reagents with Bromopyridines:Synthesis of Selectively Protected Pyridine-Containing Azamacrocycles," Journal of Organic Chemistry, (2002), vol. 67, No. 4: 1407-1410.
Nishimura, "Handbook of Heterogeneous Catalytic Hydrogenation for Organic Synthesis", John Wiley and Sons, New York, (2001), pp. 254-285.

* cited by examiner

*Primary Examiner* — John M Mauro
(74) *Attorney, Agent, or Firm* — McBee Moore & Vanik IP, LLC

(57) ABSTRACT

The present invention relates to a novel catalytic hydrogenation of substituted 2-methyl cyanopyridyl derivatives, in particular 3-chloro-5-(trifluoromethyl)pyridin-2-yl]acetonitrile [=Py-CN] to substituted 2-ethylaminopyridine derivatives, in particular 2-[3-chloro-5-(trifluoromethyl)pyridin-2-yl]ethanamine [=Py-ethanamine] or salts thereof in the presence of Raney catalysts, in particular Raney nickel or cobalt.

2 Claims, No Drawings

CATALYTIC HYDROGENATION OF NITRILES

CROSS-REFERENCE TO RELATED APPLICATIONS

This application is a National Stage entry of International Application No. PCT/EP2017/083321, filed 18 Dec. 2017, which claims priority to European Patent Application No. 16205582.6, filed 21 Dec. 2016.

BACKGROUND

Field

The present invention relates to a novel catalytic hydrogenation of substituted 2-methyl cyanopyridyl derivatives, wherein the substitution is present on the pyridine ring, in particular 3-chloro-5-(trifluoromethyl)pyridin-2-yl]acetonitrile [=Py-CN] to the corresponding substituted 2-ethylaminopyridine derivatives, in particular 2-[3-chloro-5-(trifluoromethyl)pyridin-2-yl]ethanamine [=Py-ethanamine] or salts thereof in the presence of metal catalysts such as in particular Raney catalysts.

Description of Related Art

Substituted 2-methyl cyanopyridyl derivatives, wherein the substitution is present on the pyridine ring, such as in particular 3-chloro-5-(trifluoromethyl)pyridin-2-yl]acetonitrile are important intermediates for the preparation of Fluopyram (N-[2-[3-chloro-5-(trifluoromethyl)-2-pyridinyl]ethyl]-2-(trifluoromethyl)benzamide), a commercially available fungicide, according to formula (Ia) shown below

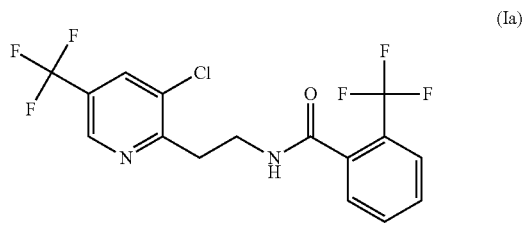 [SMILES: O=C(NCCc1ncc(C(F)(F)F)cc1Cl)c1ccccc1C(F)(F)F]

The production of Fluopyram is disclosed in WO-A 2004/16088.

In general the catalytic hydrogenation of nitriles is well known in the literature and can be carried out with different catalysts under either acidic, basic or also neutral conditions (Nishimura in "Handbook of Heterogeneous Catalytic Hydrogenation for Organic Synthesis", pp. 254-285, John Wiley and Sons, New York, 2001). It is also known that the catalytic hydrogenation of nitriles to the desired primary amines is usually accompanied by the formation of significant amounts of secondary and tertiary amines which contaminate the desired primary amine and makes the isolation very complicated, costly and inefficient and thus not suitable for being used on an industrial scale.

The catalytic hydrogenation of a substituted 2-methyl cyanopyridyl derivative to a substituted 2-ethylaminopyridine derivative according to formula (III) or its corresponding ammonium salt under hydrogen pressure in the presence of a metal catalyst in a protic solvent is described in WO 2004/016088 and EP-A 1674455. WO-A 2004/016088 and EP-A 1 674 455 disclose concretely the catalytic reduction of [3-chloro-5-(trifluoromethyl)pyridin-2-yl]acetonitrile [Py-CN] into [3-chloro-5-(trifluoromethyl)pyridin-2-yl] ethanamine [Py-ethanamine] in the presence of a palladium catalyst on charcoal in a protic solvent being acetic acid. The method described in WO-A 2004/016088 and EP-A 1 674 455 has the drawback in that the yield of the hydrogenation reaction of [Py-CN] followed by hydrolysis of the N-acetyl intermediate to [Py-ethanamine] is low. Another difficulty with this process is the potential for catalyst deactivation by the large amount of side products formed which could amount up to 60% of the end product. Side products include but are not limited to dechlorinated compounds, in particular of 2-[5-(trifluoromethyl)pyridin-2-yl]ethanamine. The low selectivity to the desired product and the formation of different side products makes the economic isolation of the compound according to formula (III) not acceptable at an industrial scale.

Raney catalysts, which are also called activated metal catalysts, comprise an alloy of at least one catalytically active metal and at least one metal that can be leached with a base. In a lot of cases aluminum is used for the alkali-soluble alloy component, but other metals such as zinc, silicium, molybdenum or chromium can also be used. By adding alkalis to the alloy the leachable component is dissolved out, due to which the catalyst becomes activated. The temperature used to leach the alloy leading to a three-dimensional mesh-like structure having pores of different sizes providing the catalyst with high thermal and structural stability and the capacity to absorb hydrogen into the pores. Examples of Raney catalysts are Raney nickel catalysts or Raney cobalt catalysts which are based on nickel alloys or cobalt-aluminium alloys which are activated in the presence of strong base like NaOH. In addition Raney catalysts are economically of interest and more readily available as they are easier to produce than supported catalysts.

It is known in the prior art to improve the hydrogenation of nitriles to the corresponding amines in the presence of an acylating agent. For example, EP-A 1 674 455 discloses a two-step synthesis of substituted 2-ethylaminopyridine derivatives comprising the catalytic reduction of reaction of a 2-methylcyanopyridine derivative in the presence of an acylating agent and of a catalyst, in a solvent, under a hydrogen pressure to provide the respective 2-ethylaminopyridyl derivative.

The catalytic hydrogenation step is performed in the presence of an excess of four equivalents of acetanhydride ($Ac_2O$). After hydrolysis of the intermediate the desired product was formed with significant amounts of side product. In addition, this method does not disclose any workup procedure nor recycling process of the expensive palladium catalyst. In addition, the reaction mixture contains large amounts of hydrochloric acid and is therefore highly corrosive. The solvent methanol reacts with the hydrochloric acid forming the gas chlormethane which is toxic and needs to be separated. Consequently the process described is disadvantageous from the economic, environmental and safety standpoint.

WO 2004/041210 relates to compounds, which are useful in the treatment of bacterial infections. Therein, the preparation of a substituted pyridinyl carbamate is mentioned, comprising the step of reacting a substituted pyridinyl acetonitrile compound to the corresponding substituted pyridinyl amine compound in THF under addition of $BH_3$-THF and HCl, followed by NaOH addition and extraction with EtOAc. However, therein no presence of a metal catalyst, particularly no palladium catalyst, is mentioned. WO 2008/125839 relates to specific pyrimidine compounds and the pharmaceutical use thereof. Therein, the preparation of 2-(6-methyl-pyridin-2-yl) ethanamine from the corresponding pyridine-2-yl acetonitrile in THF under addition of borane dimethyl sulfide complex in THF and subsequent addition of HCL is mentioned. However, therein no presence of a metal catalyst, particularly no palladium catalyst, is mentioned.

WO 2011/047156 relates to small molecule heterocyclic inhibitors of sepiapterin reductase and the medical use thereof. Therein, the reaction of a chlorine substituted pyridinyl acetonitrile compound to the corresponding chlorine substituted pyridinyl ethanamine compound in THF under addition of $BH_3$-DMS. However, therein neither acid addition nor the presence of a metal catalyst, particularly no palladium catalyst, is mentioned.

Skerlj et al. (Journal of Organic Chemistry, Vol. 67, No. 4, 2002, pages 1407-1410) relates to the synthesis of azamacrocyles, wherein the ring nitrogens are regioselectively functionalized. Therein, an organozinc palladium catalysed coupling with a functionalized bromopyridine is carried out. However, therein only a borane reduction followed by a so-called Nehishi coupling but no catalytic hydrogenation is carried out. In any case, the borane reduction reaction as described therein is not suitable in large scale production as it makes use and leads to undesired reaction products and is expensive.

None of the described prior art processes is suitable for a large scale production. In contrast, the new process of the present invention, as described in detail hereinafter, provides an economic process with significantly reduced formation of unwanted toxic side-products, particularly with reduced formation of unwanted dehalogenated side-products, and increased yield of the desired reaction products.

The chemoselective catalytic hydrogenation of nitriles according to formula (II) as disclosed below wherein at least one of the X substituents is halogen is in general problematic. Such compounds are easily dehalogenated during the catalytic hydrogenation thus forming undesired dehalogenated side-products.

A respective 2-methyl cyanopyridyl derivative according to formula (II), wherein at least one X substituent is halogen, preferably chlorine, can be defined by the following formula (II') below. Upon dehalogenation during the catalytic hydrogenation process, the corresponding dehalogenated compounds of formula (II''), as defined below, can be formed.

| Halogen substituted compound (preferably chlorine substituted compound) | corresponding dehalogenated compound (preferably dechlorinated compound) |
|---|---|
| 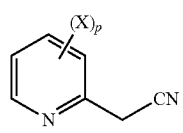<br>(II')<br>p = 1, 2, 3 or 4 | 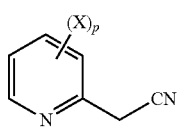<br>(II'')<br>p = 1, 2, 3 or 4 |
| each substituent X is chosen, independently of the others, as being hydrogen, halogen, $C_1$-$C_4$ alkyl or $C_1$-$C_4$ haloalkyl with the proviso that at least one substituent X is halogen, preferably chlorine | each substituent X is chosen, independently of the others, as being hydrogen, halogen, $C_1$-$C_4$ alkyl or $C_1$-$C_4$ haloalkyl with the proviso that the at least one halogen substituent, preferably chlorine substituent, of the corresponding compound (II') is replaced by hydrogen |

The tendency of a halogen-containing compound to dehalogenate during catalytic hydrogenation is higher for bromine—than for chlorine-containing compounds and higher for two- or more fold substituted compounds than for onefold substituted compounds. (cf. Nishimura in "Handbook of Heterogeneous Catalytic Hydrogenation for Organic Synthesis", pp. 623-637, John Wiley and Sons, New York, 2001). A large number of methods with different additives have been developed to reduce the hydrodehalogenation of aromatic compounds. Most of these additives have drawbacks such as low chemoselectivity, undesired side products, costs and toxicity.

It is therefore an object of the present invention to provide a novel, safer, more economically and environmentally viable process suitable for industrial scale for preparing substituted 2-ethylaminopyridine derivatives of the formula (III) from substituted 2-methyl cyanopyridyl derivatives of the formula (II), as defined below.

SUMMARY

The object was achieved according to the present invention by a process (A) for preparing substituted 2-ethylaminopyridine derivatives of the formula (III) and corresponding salts thereof,

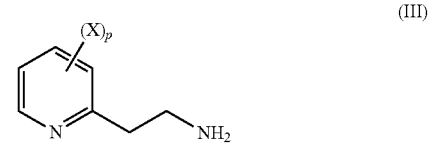
(III)

wherein p is an integer equal to 1, 2, 3 or 4;

each substituent X is chosen, independently of the others, as being halogen, $C_1$-$C_4$ alkyl or $C_1$-$C_4$ haloalkyl;

characterized in that in step (A1) a substituted 2-methyl cyanopyridyl derivative according to formula (II)

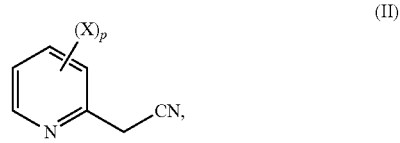
(II)

wherein p is an integer equal to 1, 2, 3 or 4;

each substituent X is chosen, independently of the others, as being halogen, $C_1$-$C_4$ alkyl or $C_1$-$C_4$ haloalkyl;

is hydrogenated in the presence of a Raney metal catalyst.

DETAILED DESCRIPTION OF A PREFERRED EMBODIMENT

Process (A) may comprise an additional step (A2) after steps (A1), wherein the isolated product according to formula (III) is reacted with a benzoyl halide according to formula (IV)

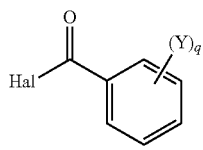

(IV)

wherein
Hal is fluorine, chlorine or bromine;
q is an integer equal to 1, 2, 3 or 4;
each substituent Y is chosen, independently of the others, as being halogen, $C_1$-$C_4$ alkyl or $C_1$-$C_4$ haloalkyl;
to the compound according to formula (I)

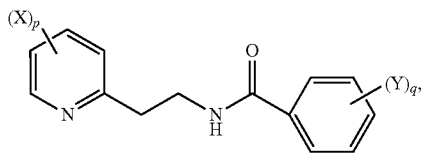

(I)

wherein p and X are defined as above;
q is an integer equal to 1, 2, 3 or 4;
each substituent Y is chosen, independently of the others, as being halogen, $C_1$-$C_4$ alkyl or $C_1$-$C_4$ haloalkyl.
p is preferably 1 or 2.
p is very preferably 2.
In each case, X is preferably independently of the others, as being fluorine, chlorine, bromine, $C_1$-$C_2$ alkyl or $C_1$-$C_2$ haloalkyl having 1 to 5 halogen atoms selected independently from each other from fluorine, chlorine;
In each case, X is more preferably independently of the others, as being fluorine, chlorine, methyl, ethyl or $C_1$-$C_2$ haloalkyl having 1 to 5 halogen atoms selected independently from each other from fluorine, chlorine;
In each case, X is particular preferably independently of the others, as being fluorine, chlorine, or difluoromethyl, trifluoromethyl, dichloromethyl, trichloromethyl;
In each case, X is very particular preferably independently of the others, as being chlorine, or trifluoromethyl.
As regards the positions in which the 2-pyridyl moiety is substituted by X, the 2-pyridyl moiety is preferably substituted by X in 3- and/or in 5-position. Preferably, the 2-pyridyl moiety is substituted by X in 3- and 5-position.
q is preferably 1 or 2.
q is very preferably 1.
Y is preferably independently of the others, as being fluorine, chlorine, bromine, $C_1$-$C_2$ alkyl or $C_1$-$C_2$ haloalkyl having 1 to 5 halogen atoms selected independently from each other from fluorine, chlorine;
Y is more preferably independently of the others, as being fluorine, chlorine, methyl, ethyl or $C_1$-$C_2$ haloalkyl having 1 to 5 halogen atoms selected independently from each other from fluorine, chlorine;
Y is particular preferably independently of the others, as being fluorine, chlorine, or difluoromethyl, trifluoromethyl, dichloromethyl, trichloromethyl;
Y is very particular preferably trifluoromethyl.
Y is very particular preferably chlorine.
As regards the positions in which the phenyl moiety is substituted by Y, the phenyl moiety is preferably substituted by Y in 2- and/or in 6-position. Preferably, the phenyl moiety is substituted by Y in 2-position.
Very particular preferably the compound according to formula (II) is 3-chloro-5-(trifluoromethyl)pyridin-2-yl]acetonitrile and the compound according to formula (III) is 2-[3-chloro-5-(trifluoromethyl)pyridin-2-yl]ethanamine.
Very preferably the compound according to formula (IV) is 2-trifluoromethyl-benzoyl chloride.
Very preferably the compound according to formula (I) is fluopyram as defined in formula (Ia).
In one embodiment the compounds according to formula (III) may be present as free amines or salts thereof.
The corresponding salts of the compounds according to formula (III) are preferably phosphates, formiates, or acetates.
In one embodiment step (A2) is performed in the presence of a base.
In another embodiment step (A2) is performed under reduced pressure without a base being present.
In another embodiment step (A2) is performed under reduced pressure and in the presence of a base.
Useful bases which may be used in the process according to the present invention, such as in particular in step (A2) are inorganic or organic bases such as $Na_2CO_3$, $NaHCO_3$, $K_2CO_3$, $KHCO_3$, NaOH, KOH, $Ca(OH)_2$, $Mg(OH)_2$, triethylamine, N,N-diisopropylethylamine, dimethylcyclohexylamine.
The following bases are particularly preferred for step (A2): $Na_2CO_3$, $NaHCO_3$, $K_2CO_3$, $KHCO_3$, NaOH, KOH, $Ca(OH)_2$. More preferred are NaOH, KOH, $Ca(OH)_2$. Mostly preferred are NaOH, KOH. Preferably, in step (A6) a base as defined herein is added until adjustment of the pH value of the reaction solution to pH 4 to 14, preferably pH 5 to 13 is achieved.
The metal catalyst is any hydrogenation catalyst selected from the group of Raney catalysts. In one embodiment the metal catalyst is a Raney catalyst selected from the group of Raney nickel and Raney cobalt.
In one embodiment the metal catalyst is any Raney cobalt catalyst.
The Raney catalysts may be present in different forms, for example as a powder, a fixed bed catalyst, as hollow spheres, extrudates, granulates, fiber tablets or shell-activated tablets
In one embodiment the Raney catalyst has a density of 0.1 to 2 g/ml.
The catalyst alloy of the catalysts used in accordance with the invention is preferably composed of up to 20-80 wt % of one or more catalytically active metals, preferably cobalt and nickel and up to 20-80 wt % of one or more alkali-leachable metals, preferably aluminum. A fast or slow cooled alloy can be used as catalyst alloy. Fast cooling is understood to mean, for example, cooling at a rate from 10 to 105 K/sec.
The cooling media can be various gases or liquids such as water. Slow cooling is understood to mean methods with lower cooling rates.
Raney catalysts doped with other metals may be used. The doping metals are frequently also called promoters. The doping of Raney catalysts is described, for example, in the documents U.S. Pat. No. 4,153,578, DE 21 01 856, DE 21 00 373 or DE 20 53 799. Preferred elements for doping are elements of groups 1A, 2A, 3B through 7B, 8, 1B, 2B and 3A of the periodic system and germanium, tin, lead, antimony and bismuth. Particularly preferred are chromium, manganese, iron, vanadium, tantalum, titanium, tungsten, molybdenum, rhenium and/or metals of the platinum group. The amount of promoters in the Raney catalyst can preferably be 0-20 wt %. The promoters can already be contained as an alloy component, or can be added only later, especially after activation.

In one embodiment hollow catalysts with a diameter from 0.05 to 20 mm and a shell thickness from 0.05 to 7 mm may be used. The catalyst shells can be impermeable, or they can have a porosity of 80% and higher.

The catalysts are available from commercial sources like the companies BASF, Acros, Evonik.

The catalysts can be used in any form, for example dry, or wet (water-wet). Preferably, the catalysts are used several times. More preferably, the catalysts are used more than two times. Most preferably, the catalysts are used between once and ten times. The catalysts can be used in in a batch, semibatch or fixed bed hydrogenation reaction as well as in a continuous hydrogenation reaction process. More preferably the catalysts can be used in in a batch or fixed bed hydrogenation reaction.

In the process according to the invention, the catalyst is used in a concentration of about 0.01 mol % to about 50 mol % catalyst with respect to the amount of cyanopyridyl derivative according to formula (II). The catalyst is preferably used in a concentration of about 0.1 to about 50 mol %, more preferably the catalyst is used in a concentration of about 0.5 mol % to about 3 mol %.

Whilst not being bound by theory, in the process of the present invention the Raney catalysts allow a reduction of the formation of the unwanted dehalogenated, particularly the dechlorinated, side-products. One the one hand, this reduces the toxicity and on the other hand enhances the yield of the desired reaction products.

By using the Raney catalyst in the process of the present invention a reduction of the dehalogenated, particularly dechlorinated, side-products is achieved, preferably to equal or less than 25%, more preferably equal or less than 20%, even more preferably equal or less than 15%, particular more preferably equal or less than 10%, even particular more preferably equal or less than 5%, most preferably equal or less than 3%, most particular preferably equal or less than 1%, can be achieved compared to the reaction as described in the prior art in WO 2004/016088 and EP-A 1674455.

The Raney cobalt catalyst may be present in different forms, for example as a powder, a fixed bed catalyst, as hollow spheres, extrudates, granulates, fiber tablets or shell-activated tablets.

In one embodiment the Raney cobalt catalyst has a density of 0.1 to 2 g/ml.

The catalyst alloy of the catalysts used in accordance with the invention is preferably composed of up to 20-80 wt % of one or more catalytically active metals, preferably cobalt and nickel and up to 20-80 wt % of one or more alkali-leachable metals, preferably aluminum. A fast or slow cooled alloy can be used as catalyst alloy. Fast cooling is understood to mean, for example, cooling at a rate from 10 to 105 K/sec. The cooling media can be various gases or liquids such as water. Slow cooling is understood to mean methods with lower cooling rates.

Raney cobalt catalyst doped with other metals may be used. The doping metals are frequently also called promoters. The doping of Raney cobalt catalyst is described, for example, in the documents U.S. Pat. No. 4,153,578, DE 21 01 856, DE 21 00 373 or DE 20 53 799. Preferred elements for doping are elements of groups 1A, 2A, 3B through 7B, 8, 1B, 2B and 3A of the periodic system and germanium, tin, lead, antimony and bismuth. Particularly preferred are chromium, manganese, iron, vanadium, tantalum, titanium, tungsten, molybdenum, rhenium and/or metals of the platinum group. The amount of promoters in the Raney cobalt catalyst can preferably be 0-20 wt %. The promoters can already be contained as an alloy component, or can be added only later, especially after activation.

In one embodiment hollow catalysts with a diameter from 0.05 to 20 mm and a shell thickness from 0.05 to 7 mm may be used. The catalyst shells can be impermeable, or they can have a porosity of 80% and higher.

The catalysts are available from commercial sources like the companies BASF, Acros, Evonik.

The catalysts can be used in any form, for example dry, or wet (water-wet). Preferably, the catalysts are used several times. More preferably, the catalysts are used more than two times. Most preferably, the catalysts are used between once and ten times. The catalysts can be used in in a batch, semibatch or fixed bed hydrogenation reaction as well as in a continuous hydrogenation reaction process. More preferably the catalysts can be used in in a batch or fixed bed hydrogenation reaction.

In the process according to the invention, the catalyst is used in a concentration of about 0.01 mol % to about 50 mol % catalyst with respect to the amount of cyanopyridyl derivative according to formula (II). The catalyst is preferably used in a concentration of about 0.1 to about 50 mol %, more preferably the catalyst is used in a concentration of about 0.5 mol % to about 3 mol %.

Whilst not being bound by theory, in the process of the present invention the Raney cobalt catalyst allow a reduction of the formation of the unwanted dehalogenated, particularly the dechlorinated, side-products.

One the one hand, this reduces the toxicity and on the other hand enhances the yield of the desired reaction products.

By using the Raney cobalt catalyst in the process of the present invention a reduction of the dehalogenated, particularly dechlorinated, side-products is achieved, preferably to equal or less than 25%, more preferably equal or less than 20%, even more preferably equal or less than 15%, particular more preferably equal or less than 10%, even particular more preferably equal or less than 5%, most preferably equal or less than 3%, most particular preferably equal or less than 1%, can be achieved compared to the reaction as described in the prior art in WO 2004/016088 and EP-A 1674455.

The Raney nickel catalyst may be present in different forms, for example as a powder, a fixed bed catalyst, as hollow spheres, extrudates, granulates, fiber tablets or shell-activated tablets In one embodiment the Raney nickel catalyst has a density of 0.1 to 2 g/ml.

The catalyst alloy of the catalysts used in accordance with the invention is preferably composed of up to 20-80 wt % of one or more catalytically active metals, preferably cobalt and nickel and up to 20-80 wt % of one or more alkali-leachable metals, preferably aluminum. A fast or slow cooled alloy can be used as catalyst alloy. Fast cooling is understood to mean, for example, cooling at a rate from 10 to 105 K/sec. The cooling media can be various gases or liquids such as water. Slow cooling is understood to mean methods with lower cooling rates.

Raney nickel catalyst doped with other metals may be used. The doping metals are frequently also called promoters. The doping of Raney nickel catalyst is described, for example, in the documents U.S. Pat. No. 4,153,578, DE 21 01 856, DE 21 00 373 or DE 20 53 799. Preferred elements for doping are elements of groups 1A, 2A, 3B through 7B, 8, 1B, 2B and 3A of the periodic system and germanium, tin, lead, antimony and bismuth. Particularly preferred are chromium, manganese, iron, vanadium, tantalum, titanium, tungsten, molybdenum, rhenium and/or metals of the platinum group. The amount of promoters in the Raney nickel catalyst can preferably be 0-20 wt %. The promoters can already be contained as an alloy component, or can be added only later, especially after activation.

In one embodiment hollow catalysts with a diameter from 0.05 to 20 mm and a shell thickness from 0.05 to 7 mm may be used. The catalyst shells can be impermeable, or they can have a porosity of 80% and higher.

The catalysts are available from commercial sources like the companies BASF, Acros, Evonik.

The catalysts can be used in any form, for example dry, or wet (water-wet). Preferably, the catalysts are used several times. More preferably, the catalysts are used more than two times. Most preferably, the catalysts are used between once and ten times. The catalysts can be used in in a batch, semibatch or fixed bed hydrogenation reaction as well as in a continuous hydrogenation reaction process. More preferably the catalysts can be used in in a batch or fixed bed hydrogenation reaction.

In the process according to the invention, the catalyst is used in a concentration of about 0.01 mol % to about 50 mol % catalyst with respect to the amount of cyanopyridyl derivative according to formula (II). The catalyst is preferably used in a concentration of about 0.1 to about 50 mol %, more preferably the catalyst is used in a concentration of about 0.5 mol % to about 3 mol %.

Whilst not being bound by theory, in the process of the present invention the Raney nickel catalyst allow a reduction of the formation of the unwanted dehalogenated, particularly the dechlorinated, side-products.

One the one hand, this reduces the toxicity and on the other hand enhances the yield of the desired reaction products.

By using the Raney nickel catalyst in the process of the present invention a reduction of the dehalogenated, particularly dechlorinated, side-products is achieved, preferably to equal or less than 25%, more preferably equal or less than 20%, even more preferably equal or less than 15%, particular more preferably equal or less than 10%, even particular more preferably equal or less than 5%, most preferably equal or less than 3%, most particular preferably equal or less than 1%, can be achieved compared to the reaction as described in the prior art in WO 2004/016088 and EP-A 1674455.

The hydrogenation reaction can be conducted at any suitable reaction conditions. In general the hydrogenation reaction will be conducted under batch, semi/batch or fixed bed conditions as well as in a continuous hydrogenation reaction process.

In one embodiment the hydrogenation reaction will be conducted under batch or fixed bed conditions.

Therein, the hydrogenation reaction is performed in either batch, semi-batch or continuous slurry reactors. Semi-batch hydrogenation involves the feeding of the nitrile to a slurry of catalyst in a solvent (or without). In this mode the ratio of nitrile to the catalyst is lower compared to batch process. In contrast to the batch or semi-batch process in the continuous mode the product is removed at the same rate as nitrile is added.

Pressure

The catalytic hydrogenation according to the invention is preferably performed under elevated pressure (i.e. up to about 600 bar), preferably in an autoclave in a hydrogen gas atmosphere, preferably in a semi batch hydrogenation process. The (additional) pressure increase can be brought about by supply of an inert gas, such as nitrogen or argon. The hydrogenation according to the invention is effected preferably at a hydrogen pressure in the range from about 0 to about 300 bar, more preferably at a hydrogen pressure in the range from about 5 to about 200 bar. Preferred ranges of hydrogen pressure are also e from about 0.5 to about 50 bar.

In one embodiment the catalytic hydrogenation according to the invention is preferably performed under elevated pressure (i.e. up to about 200 bar).

The hydrogen pressure according to the invention can also vary during the process.

If necessary, suitable measures for dissipating heat from the exothermic reaction can be applied.

Temperature

The catalytic hydrogenation according to the invention is performed preferably at a temperature in the range from about −20° C. to about 200° C., more preferably at a temperature in the range from about 0° C. to about 100° C., most preferably in the range from about 5 to 70° C.

Solvents

The catalytic hydrogenation can also be performed without a solvent. However, it is generally advantageous to perform the process according to the invention in the presence of solvents (diluents). Solvents are advantageously used in such an amount that the reaction mixture remains efficiently stirrable over the entire process. Advantageously, based on the nitrile used, 1 to 50 times the amount of solvent, preferably 2 to 40 times the amount of solvent and more preferably 2 to 30 times the amount of solvent is used.

Useful solvents for the performance of the hydrogenation process according to the invention include water and all organic solvents which are inert under the reaction conditions, the type of solvent used depending on the type of reaction procedure, more particularly on the type of catalyst used and/or the hydrogen source (introduction of gaseous hydrogen or generation in situ). Solvents are also understood in accordance with the invention to mean mixtures of pure solvents.

Solvents suitable in accordance to the invention are water, acids such as acetic acid, acetic anhydride, alcohols such as methanol, ethanol, isopropanol, 1-propanol, butanol, tert. butanol, 1-butanol, 2-butanol, t-amyl alcohol, benzyl alcohol, 1,3-butanediol, 1,4-butanediol, 2-butoxyethanol, cyclohexanol, diethylene glycol, diethylen glycol methyl ether, dipropylene glycol, dipropylene glycol methyl ether, 2-ethoxyethanol, ethanolamine, ethylene glycol, glycerol, hexanole, hexylene glycol, isoamyl alcohol, isobutanol, 2-methoxyethanol, 1-octanol, pentanol, propylene glycol, tetraethylene glycol, triethylene glycol; ethers, such as ethyl propyl ether, methyl tert-butyl ether, n-butyl ether, anisole, phenetole, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, methyl tetrahydrofuran, methyl cyclopenthylether, dioxane, dichlorodiethyl ether, petroleum ether, ligroin and polyethers of ethylene oxide and/or propylene oxide; ketones such as acetone, cyclohexanone, 3-pentanone, amines, such as trimethyl-, triethyl-, tripropyl-, and tributylamine, tert-amyl methyl ether (TAME), N-methyl morpholine, aliphatic, cycloaliphatic or aromatic hydrocarbons such as pentane, hexane, methyl cyclohexane heptane, octane, nonane, and technical-grade hydrocarbons which may be substituted by fluorine and chlorine atoms, such as dichloromethane, fluorobenzene, chlorobenzene or dichlorobenzene, for example white spirits having components with boiling points in the range, for example, from 40° C. to 250° C., cymene, petroleum fractions within a boiling range from 70° C. to 190° C., toluene, xylenes, ethylbenzene. esters such as amyl acetates, butyl acetates, ethyl acetate, isobutyl acetate, isopropyl acetate, 2-methoxyethyl acetate, methyl acetate, propyl acetate, prop glycol methyl ether acetate, carbonate such as propylene carbonate, dimethyl carbonate, diethyl carbonate; N,N-Dimethylacetimide, N,N-Dimethylformamide, 2-pyrrolidone and N-methyl pyrrolidone.

In the process according to the invention, it is preferred to use alcohols, esters or ethers as solvent. Preferred are methanol, ethanol, isopropanol, 1-propanol, butanol, tert. butanol, 1-butanol, 2-butanol, t-amyl alcohol, benzyl alcohol, 1,3-butanediol, 1,4-butandiol, 2-butoxyethanol, cyclohexanol, diethylene glycol, methyl-tert-butyl ether, amyl acetates, butyl acetates, ethyl acetate, isobutyl acetate, isopropyl acetate, 2-methoxyethyl acetate, methyl acetate, propyl acetate, prop glycol methyl ether acetate.

The solvents which can be used in step (A1) can be the same or different and can independently in each case be used as mixtures of solvents, in particular mixtures comprising water or as solvents consisting of only one component.

EXAMPLES

The examples shown below further illustrate the invention without limiting it.

Examples regarding Process (A):

Example 1: Hydrogenation with Raney Cobalt Catalyst

The water-comprising Raney cobalt catalyst (Actimet Cobalt (BASF)) is washed three times with water and another three times with tert-butyl methyl ether (MTBE).

An autoclave is charged with 30% (w/w) of the washed Raney cobalt catalyst and 66 g of [3-chloro-5-(trifluoromethyl)pyridin-2-yl]acetonitrile solved in 340 g of MTBE. Another 50 g of MTBE is added. The contents are then stirred at an elevated hydrogen pressure of 20 bar at 25° C. until the hydrogen uptake ceased after about three hours. Stirring is then continued for another hour. The reaction mixture is removed by filtration from the autoclave. The removed reaction mixture is analyzed by HPLC to quantify the content of amine.

The product 2-[3-chloro-5-(trifluoromethyl)pyridin-2-yl]ethanamine was obtained at 76.59% yield in a first example, and at 74.74% in a second example.

The invention claimed is:

1. A process for preparing 2-[3-chloro-5-(trifluoromethyl)pyridin-2-yl]ethanamine or corresponding salts thereof, comprising
   (A1) hydrogenating [3-chloro-5-(trifluoromethyl)pyridin-2-yl]acetonitrile in the presence of Raney cobalt catalyst.

2. The process according to claim 1 further comprising (A2) reacting the 2-[3-chloro-5-(trifluoromethyl)pyridin-2-yl]ethanamine obtained in step (A1) with a benzoyl halide according to formula (IV)

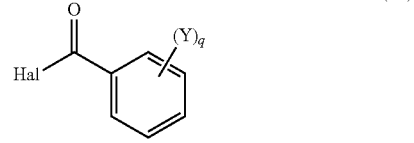

(IV)

wherein
   Hal is fluorine, chlorine or bromine;
   q is an integer equal to 1, 2, 3 or 4; and each substituent Y is chosen, independently of the others, as being halogen,
   $C_1$-$C_4$ alkyl or $C_1$-$C_4$ haloalkyl; to produce a compound having the formula

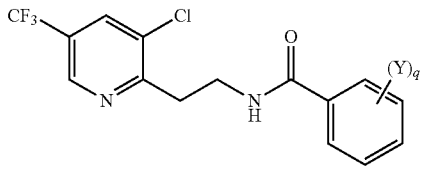

wherein
   q is an integer equal to 1, 2, 3 or 4; and
   each substituent Y is independently halogen,
   $C_1$-$C_4$ alkyl or $C_1$-$C_4$ haloalkyl.

* * * * *